(12) United States Patent
Seifert et al.

(10) Patent No.: US 11,179,246 B2
(45) Date of Patent: *Nov. 23, 2021

(54) INTERVERTEBRAL IMPLANT

(71) Applicant: GLOBUS MEDICAL, INC., Audubon, PA (US)

(72) Inventors: Jody L. Seifert, Birdsboro, PA (US); Michal Zentko, Florham Park, NJ (US); Andrew Iott, Newtown Square, PA (US); Christopher Angelucci, Schwenksville, PA (US); Chad Glerum, Pennsburg, PA (US); Ryan Watt, Boyertown, PA (US)

(73) Assignee: Globus Medical, Inc., Audubon, PA (US)

( * ) Notice: Subject to any disclaimer, the term of this patent is extended or adjusted under 35 U.S.C. 154(b) by 127 days.

This patent is subject to a terminal disclaimer.

(21) Appl. No.: 16/574,908

(22) Filed: Sep. 18, 2019

(65) Prior Publication Data
US 2020/0030111 A1 Jan. 30, 2020

Related U.S. Application Data (63) Continuation of application No. 15/864,447, filed on Jan. 8, 2018, now Pat. No. 10,456,269, which is a
(Continued)

(51) Int. Cl.
*A61F 2/44* (2006.01)
*A61B 17/86* (2006.01)
(Continued)

(52) U.S. Cl.
CPC .............. *A61F 2/447* (2013.01); *A61F 2/442* (2013.01); *A61F 2/4465* (2013.01); *A61B 17/86* (2013.01);
(Continued)

(58) Field of Classification Search
CPC ........ A61F 2/447; A61F 2/442; A61F 2/4465; A61F 2/30; A61F 2/4684;
(Continued)

(56) References Cited

U.S. PATENT DOCUMENTS

| 1,673,630 A | 6/1928 | Madge |
| 4,349,921 A | 9/1982 | Kuntz |

(Continued)

FOREIGN PATENT DOCUMENTS

| FR | 2727003 A1 | 5/1996 |
| WO | 1997023175 A1 | 7/1997 |

(Continued)

OTHER PUBLICATIONS

Guidance Document: Intervertebral Body Fusion Device, U.S. Dept. of Health and Human Services, Food and Drug Administration (Jun. 12, 2007).

(Continued)

*Primary Examiner* — Pedro Philogene (57) ABSTRACT

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides holes extending from a side portion to the inferior and superior surfaces of the spacer portion and a plate portion rigidly coupled to the spacer portion, wherein the plate portion contains holes for receiving screws. A fastener back out prevention mechanism adapted on the
(Continued)

plate to prevent the back out of the fasteners from the holes and to secure the spacer to the plate of the intervertebral implant.

20 Claims, 6 Drawing Sheets

Related U.S. Application Data continuation of application No. 14/848,827, filed on Sep. 9, 2015, now Pat. No. 9,895,237, which is a continuation of application No. 12/756,438, filed on Apr. 8, 2010, now Pat. No. 9,155,631.

(51) Int. Cl.
  A61F 2/30      (2006.01)
  A61F 2/46      (2006.01)
  A61F 2/28      (2006.01)

(52) U.S. Cl.
  CPC ............... *A61F 2/30* (2013.01); *A61F 2/4684* (2013.01); *A61F 2002/2835* (2013.01); *A61F 2002/305* (2013.01); *A61F 2002/3008* (2013.01); *A61F 2002/3081* (2013.01); *A61F 2002/30401* (2013.01); *A61F 2002/30482* (2013.01); *A61F 2002/30494* (2013.01); *A61F 2002/30507* (2013.01); *A61F 2002/30517* (2013.01); *A61F 2002/30522* (2013.01); *A61F 2002/30578* (2013.01); *A61F 2002/30593* (2013.01); *A61F 2002/30604* (2013.01); *A61F 2002/30622* (2013.01); *A61F 2002/30808* (2013.01); *A61F 2002/30843* (2013.01); *A61F 2002/30878* (2013.01); *A61F 2002/30904* (2013.01); *A61F 2310/00023* (2013.01)

(58) Field of Classification Search
  CPC .... A61F 2310/00023; A61F 2002/2835; A61F 2002/3008; A61F 2002/30401; A61F 2002/30482; A61F 2002/30492; A61F 2002/305; A61F 2002/30507; A61F 2002/30517; A61F 2002/30522; A61F 2002/30578; A61F 2002/30593; A61F 2002/30604; A61F 2002/30622; A61F 2002/30808; A61F 2002/3081; A61F 2002/30843; A61F 2002/30878; A61F 2002/30904; A61B 17/86
  USPC .............................. 623/17.11–17.16
  See application file for complete search history.

(56) References Cited

U.S. PATENT DOCUMENTS

| | | |
|---|---|---|
| 4,599,086 A | 7/1986 | Doty |
| 4,743,256 A | 5/1988 | Brantigan |
| 4,834,757 A | 5/1989 | Brantigan |
| 4,904,261 A | 2/1990 | Dove et al. |
| 4,917,704 A | 4/1990 | Frey |
| 4,955,908 A | 9/1990 | Frey |
| 5,002,576 A | 3/1991 | Fuhrmann et al. |
| 5,163,949 A | 11/1992 | Bonutti |
| 5,163,960 A | 11/1992 | Bonutti |
| 5,197,971 A | 3/1993 | Bonutti |
| 5,269,785 A | 12/1993 | Bonutti |
| 5,295,994 A | 3/1994 | Bonutti |
| 5,329,846 A | 7/1994 | Bonutti |
| 5,331,975 A | 7/1994 | Bonutti |
| 5,345,927 A | 9/1994 | Bonutti |
| 5,364,399 A | 11/1994 | Lowery et al. |
| 5,397,364 A | 3/1995 | Kozak et al. |
| 5,403,317 A | 4/1995 | Bonutti |
| 5,403,348 A | 4/1995 | Bonutti |
| 5,441,538 A | 8/1995 | Bonutti |
| 5,454,365 A | 10/1995 | Bonutti |
| 5,458,641 A | 10/1995 | Jiminez |
| 5,464,426 A | 11/1995 | Bonutti |
| 5,496,348 A | 3/1996 | Bonutti |
| 5,514,153 A | 5/1996 | Bonutti |
| 5,514,180 A | 5/1996 | Heggeness |
| 5,522,846 A | 6/1996 | Bonutti |
| 5,527,343 A | 6/1996 | Bonutti |
| 5,534,012 A | 7/1996 | Bonutti |
| 5,545,222 A | 8/1996 | Bonutti |
| 5,549,612 A | 8/1996 | Yapp et al. |
| 5,549,630 A | 8/1996 | Bonutti |
| 5,549,631 A | 8/1996 | Bonutti |
| 5,569,305 A | 10/1996 | Bonutti |
| 5,577,517 A | 11/1996 | Bonutti |
| 5,584,862 A | 12/1996 | Bonutti |
| 5,593,425 A | 1/1997 | Bonutti |
| 5,624,462 A | 4/1997 | Bonutti |
| 5,645,596 A | 7/1997 | Kim et al. |
| 5,662,710 A | 9/1997 | Bonutti |
| 5,667,520 A | 9/1997 | Bonutti |
| 5,685,826 A | 11/1997 | Bonutti |
| 5,694,951 A | 12/1997 | Bonutti |
| 5,707,390 A | 1/1998 | Bonutti |
| 5,716,325 A | 2/1998 | Bonutti |
| 5,733,306 A | 3/1998 | Bonutti |
| 5,735,875 A | 4/1998 | Bonutti |
| 5,827,318 A | 10/1998 | Bonutti |
| 5,845,645 A | 12/1998 | Bonutti |
| 5,860,997 A | 1/1999 | Bonutti |
| 5,861,041 A | 1/1999 | Tienboon |
| 5,888,196 A | 3/1999 | Bonutti |
| 5,888,219 A | 3/1999 | Bonutti |
| 5,888,223 A | 3/1999 | Bray, Jr. |
| 5,928,267 A | 7/1999 | Bonutti |
| 5,935,131 A | 8/1999 | Bonutti |
| 5,941,900 A | 8/1999 | Bonutti |
| 5,954,739 A | 9/1999 | Bonutti |
| 6,010,525 A | 1/2000 | Bonutti |
| 6,017,305 A | 1/2000 | Bonutti |
| 6,042,596 A | 3/2000 | Bonutti |
| 6,045,579 A | 4/2000 | Hochshuler |
| 6,059,817 A | 5/2000 | Bonutti |
| 6,066,175 A | 5/2000 | Henderson et al. |
| 6,077,292 A | 6/2000 | Bonutti |
| 6,086,593 A | 7/2000 | Bonutti |
| 6,099,531 A | 8/2000 | Bonutti |
| 6,102,928 A | 8/2000 | Bonutti |
| 6,132,472 A | 10/2000 | Bonutti |
| RE36,974 E | 11/2000 | Bonutti |
| 6,146,421 A | 11/2000 | Gordon |
| 6,156,037 A | 12/2000 | LeHuec et al. |
| 6,159,234 A | 12/2000 | Bonutti |
| 6,171,236 B1 | 1/2001 | Bonutti |
| 6,171,299 B1 | 1/2001 | Bonutti |
| 6,174,313 B1 | 1/2001 | Bonutti |
| 6,187,023 B1 | 2/2001 | Bonutti |
| 6,200,347 B1 | 3/2001 | Anderson et al. |
| 6,203,565 B1 | 3/2001 | Bonutti |
| 6,206,922 B1 | 3/2001 | Zdeblick et al. |
| 6,217,617 B1 | 4/2001 | Bonutti |
| 6,231,592 B1 | 5/2001 | Bonutti |
| 6,231,610 B1 | 5/2001 | Geisler |
| 6,235,059 B1 | 5/2001 | Benezech |
| 6,258,089 B1 | 7/2001 | Campbell et al. |
| 6,277,136 B1 | 8/2001 | Bonutti |
| 6,287,325 B1 | 9/2001 | Bonutti |
| 6,342,074 B1 | 1/2002 | Simpson |
| 6,358,266 B1 | 3/2002 | Bonutti |
| 6,361,565 B1 | 3/2002 | Bonutti |
| 6,364,880 B1 | 4/2002 | Michelson |
| 6,368,343 B1 | 4/2002 | Bonutti |
| 6,383,186 B1 | 5/2002 | Michelson |
| 6,425,920 B1 | 7/2002 | Hamada |
| 6,432,106 B1 | 8/2002 | Fraser |
| 6,447,516 B1 | 9/2002 | Bonutti |

(56) References Cited

U.S. PATENT DOCUMENTS

| | | |
|---|---|---|
| 6,451,042 B1 | 9/2002 | Bonutti |
| 6,464,713 B2 | 10/2002 | Bonutti |
| 6,468,289 B1 | 10/2002 | Bonutti |
| 6,468,293 B2 | 10/2002 | Bonutti |
| 6,471,724 B2 | 10/2002 | Zdeblick |
| 6,475,230 B1 | 11/2002 | Bonutti |
| 6,482,233 B1 | 11/2002 | Aebi |
| 6,500,195 B2 | 12/2002 | Bonutti |
| 6,503,267 B2 | 1/2003 | Bonutti |
| 6,503,277 B2 | 1/2003 | Bonutti |
| 6,520,993 B2 | 2/2003 | James |
| 6,540,785 B1 | 4/2003 | Gill et al. |
| 6,543,455 B2 | 4/2003 | Bonutti |
| 6,558,387 B2 | 5/2003 | Errico |
| 6,558,423 B1 | 5/2003 | Michelson |
| 6,558,424 B2 | 5/2003 | Thalgott |
| 6,562,073 B2 | 5/2003 | Foley |
| 6,569,187 B1 | 5/2003 | Bonutti |
| 6,575,982 B1 | 6/2003 | Bonutti |
| 6,585,750 B2 | 7/2003 | Bonutti |
| 6,592,531 B2 | 7/2003 | Bonutti |
| 6,592,609 B1 | 7/2003 | Bonutti |
| 6,607,534 B2 | 8/2003 | Bonutti |
| 6,620,181 B1 | 9/2003 | Bonutti |
| 6,629,998 B1 | 10/2003 | Lin |
| 6,630,000 B1 | 10/2003 | Bonutti |
| 6,635,073 B2 | 10/2003 | Bonutti |
| 6,638,309 B2 | 10/2003 | Bonutti |
| 6,652,532 B2 | 11/2003 | Bonutti |
| 6,666,889 B1 | 12/2003 | Commarmond |
| 6,682,563 B2 | 1/2004 | Scharf |
| 6,702,821 B2 | 3/2004 | Bonutti |
| 6,702,856 B2 | 3/2004 | Bonutti |
| 6,709,458 B2 | 3/2004 | Michelson |
| 6,719,803 B2 | 4/2004 | Bonutti |
| 6,730,127 B2 | 5/2004 | Michelson |
| 6,736,853 B2 | 5/2004 | Bonutti |
| 6,740,118 B2 | 5/2004 | Eisermann et al. |
| 6,770,078 B2 | 8/2004 | Bonutti |
| 6,776,938 B2 | 8/2004 | Bonutti |
| 6,793,658 B2 | 9/2004 | Lehuec |
| 6,805,714 B2 | 10/2004 | Sutcliffe |
| 6,827,740 B1 | 12/2004 | Michelson |
| 6,835,198 B2 | 12/2004 | Bonutti |
| 6,835,206 B2 | 12/2004 | Jackson |
| 6,849,093 B2 | 2/2005 | Michelson |
| 6,860,885 B2 | 3/2005 | Bonutti |
| 6,860,904 B2 | 3/2005 | Bonutti |
| 6,887,272 B2 | 5/2005 | Shinomiya |
| 6,899,735 B2 | 5/2005 | Coates et al. |
| 6,905,517 B2 | 6/2005 | Bonutti |
| 6,908,466 B1 | 6/2005 | Bonutti |
| 6,932,835 B2 | 8/2005 | Bonutti |
| 6,972,019 B2 | 12/2005 | Michelson |
| 6,989,029 B2 | 1/2006 | Bonutti |
| 6,990,982 B1 | 1/2006 | Bonutti |
| 7,001,432 B2 | 2/2006 | Keller et al. |
| 7,025,787 B2 | 4/2006 | Bryan et al. |
| 7,044,972 B2 | 5/2006 | Mathys, Jr. |
| 7,048,755 B2 | 5/2006 | Bonutti |
| 7,070,557 B2 | 7/2006 | Bonutti |
| 7,087,073 B2 | 8/2006 | Bonutti |
| 7,094,251 B2 | 8/2006 | Bonutti |
| 7,104,996 B2 | 9/2006 | Bonutti |
| 7,114,500 B2 | 10/2006 | Bonutti |
| 7,128,753 B1 | 10/2006 | Bonutti |
| 7,134,437 B2 | 11/2006 | Bonutti |
| 7,137,997 B2 | 11/2006 | Paul |
| 7,147,652 B2 | 12/2006 | Bonutti |
| 7,147,665 B1 | 12/2006 | Bryan et al. |
| 7,153,325 B2 | 12/2006 | Kim et al. |
| 7,163,561 B2 | 1/2007 | Michelson |
| 7,172,627 B2 | 2/2007 | Fiere et al. |
| 7,192,447 B2 | 3/2007 | Rhoda |
| 7,208,013 B1 | 4/2007 | Bonutti |
| 7,217,273 B2 | 5/2007 | Bonutti |
| 7,217,290 B2 | 5/2007 | Bonutti |
| 7,232,464 B2 | 6/2007 | Matthieu et al. |
| 7,238,203 B2 | 7/2007 | Bagga et al. |
| 7,276,082 B2 | 10/2007 | Zdeblick et al. |
| 7,309,357 B2 | 12/2007 | Kim |
| 7,311,719 B2 | 12/2007 | Bonutti |
| 7,320,708 B1 | 1/2008 | Bernstein |
| 7,329,263 B2 | 2/2008 | Bonutti |
| 7,429,266 B2 | 9/2008 | Bonutti |
| 7,462,200 B2 | 12/2008 | Bonutti |
| 7,481,831 B2 | 1/2009 | Bonutti |
| 7,510,557 B1 | 3/2009 | Bonutti |
| 7,594,931 B2 | 9/2009 | Louis et al. |
| 7,615,054 B1 | 11/2009 | Bonutti |
| 7,618,456 B2 | 11/2009 | Matthieu |
| 7,635,390 B1 | 12/2009 | Bonutti |
| 7,708,740 B1 | 5/2010 | Bonutti |
| 7,708,741 B1 | 5/2010 | Bonutti |
| 7,727,283 B2 | 6/2010 | Bonutti |
| 7,749,229 B1 | 7/2010 | Bonutti |
| 7,771,475 B2 | 8/2010 | Michelson |
| 7,780,670 B2 | 8/2010 | Bonutti |
| 7,794,502 B2 | 9/2010 | Michelson |
| 7,806,896 B1 | 10/2010 | Bonutti |
| 7,806,897 B1 | 10/2010 | Bonutti |
| 7,828,852 B2 | 11/2010 | Bonutti |
| 7,837,736 B2 | 11/2010 | Bonutti |
| 7,846,207 B2 * | 12/2010 | Lechmann ............ A61F 2/4465 623/17.11 |
| 7,850,731 B2 | 12/2010 | Brittain |
| 7,854,750 B2 | 12/2010 | Bonutti |
| 7,862,616 B2 | 1/2011 | Lechmann |
| 7,875,076 B2 | 1/2011 | Matthieu |
| 7,879,072 B2 | 2/2011 | Bonutti |
| 7,892,236 B1 | 2/2011 | Bonutti |
| 7,892,261 B2 | 2/2011 | Bonutti |
| 7,896,880 B2 | 3/2011 | Bonutti |
| 7,931,690 B1 | 4/2011 | Bonutti |
| 7,959,635 B1 | 6/2011 | Bonutti |
| 7,972,381 B2 | 7/2011 | Michelson |
| 8,100,976 B2 | 1/2012 | Bray et al. |
| 8,105,383 B2 | 1/2012 | Michelson |
| 8,114,162 B1 | 2/2012 | Bradley |
| 8,128,669 B2 | 3/2012 | Bonutti |
| 8,133,229 B1 | 3/2012 | Bonutti |
| 8,137,405 B2 | 3/2012 | Kostuik et al. |
| 8,162,977 B2 | 4/2012 | Bonutti |
| 8,216,312 B2 | 7/2012 | Gray |
| 8,268,000 B2 | 9/2012 | Waugh et al. |
| 8,323,343 B2 | 12/2012 | Michelson |
| 8,328,872 B2 * | 12/2012 | Duffield .................. A61F 2/44 623/17.16 |
| 8,343,222 B2 | 1/2013 | Cope |
| 8,425,522 B2 | 4/2013 | Bonutti |
| 8,425,607 B2 | 4/2013 | Waugh et al. |
| 8,439,977 B2 | 5/2013 | Kostuik et al. |
| 8,486,066 B2 | 7/2013 | Bonutti |
| 8,540,774 B2 * | 9/2013 | Kueenzi ................ A61F 2/4425 623/17.16 |
| 8,623,030 B2 | 1/2014 | Bonutti |
| 8,632,552 B2 | 1/2014 | Bonutti |
| 8,641,726 B2 | 2/2014 | Bonutti |
| 8,690,944 B2 | 4/2014 | Bonutti |
| 8,739,797 B2 | 6/2014 | Bonutti |
| 8,747,439 B2 | 6/2014 | Bonutti |
| 8,784,495 B2 | 7/2014 | Bonutti |
| 8,795,363 B2 | 8/2014 | Bonutti |
| 8,814,902 B2 | 8/2014 | Bonutti |
| 8,834,490 B2 | 9/2014 | Bonutti |
| 8,840,629 B2 | 9/2014 | Bonutti |
| 8,845,699 B2 | 9/2014 | Bonutti |
| 8,858,557 B2 | 10/2014 | Bonutti |
| 8,956,417 B2 | 2/2015 | Bonutti |
| 9,044,322 B2 | 6/2015 | Bonutti |
| 9,044,341 B2 | 6/2015 | Bonutti |
| 9,050,152 B2 | 6/2015 | Bonutti |
| 9,192,419 B2 * | 11/2015 | McDonough ...... A61B 17/7059 |
| 10,456,269 B2 * | 10/2019 | Seifert .................... A61F 2/447 |

(56) References Cited

U.S. PATENT DOCUMENTS

| | | |
|---|---|---|
| 2001/0005796 A1 | 6/2001 | Zdeblick |
| 2001/0023371 A1 | 9/2001 | Bonutti |
| 2001/0034553 A1 | 10/2001 | Michelson |
| 2002/0004683 A1 | 1/2002 | Michelson |
| 2002/0010511 A1 | 1/2002 | Michelson |
| 2002/0016595 A1 | 2/2002 | Michelson |
| 2002/0029055 A1 | 3/2002 | Bonutti |
| 2002/0040246 A1 | 4/2002 | Bonutti |
| 2002/0082597 A1 | 6/2002 | Fraser |
| 2002/0095160 A1 | 7/2002 | Bonutti |
| 2002/0138146 A1 | 9/2002 | Jackson |
| 2002/0143399 A1 | 10/2002 | Sutcliffe |
| 2002/0147450 A1 | 10/2002 | Lehuec |
| 2003/0009147 A1 | 1/2003 | Bonutti |
| 2003/0023260 A1 | 1/2003 | Bonutti |
| 2003/0045939 A1 | 3/2003 | Casutt |
| 2003/0105528 A1 | 6/2003 | Shimp et al. |
| 2003/0125739 A1 | 7/2003 | Bagga |
| 2003/0167091 A1 | 9/2003 | Scharf |
| 2003/0181981 A1 | 9/2003 | Lemaire |
| 2004/0010287 A1 | 1/2004 | Bonutti |
| 2004/0078078 A1 | 4/2004 | Shepard |
| 2004/0082998 A1 | 4/2004 | Shinomiya |
| 2004/0082999 A1 | 4/2004 | Robert, Jr. |
| 2004/0097794 A1 | 5/2004 | Bonutti |
| 2004/0098016 A1 | 5/2004 | Bonutti |
| 2004/0117018 A1 | 6/2004 | Michelson |
| 2004/0138689 A1 | 7/2004 | Bonutti |
| 2004/0138690 A1 | 7/2004 | Bonutti |
| 2004/0143270 A1 | 7/2004 | Zucherman |
| 2004/0143285 A1 | 7/2004 | Bonutti |
| 2004/0143332 A1 | 7/2004 | Krueger et al. |
| 2004/0172033 A1 | 9/2004 | Bonutti |
| 2004/0176853 A1 | 9/2004 | Sennett et al. |
| 2004/0193181 A1 | 9/2004 | Bonutti |
| 2004/0230223 A1 | 11/2004 | Bonutti |
| 2005/0055098 A1 | 3/2005 | Zdeblick et al. |
| 2005/0065607 A1 | 3/2005 | Gross |
| 2005/0149192 A1 | 7/2005 | Zucherman et al. |
| 2005/0149193 A1 | 7/2005 | Zuchermann et al. |
| 2005/0159819 A1 | 7/2005 | McCormack et al. |
| 2005/0171607 A1 | 8/2005 | Michelson |
| 2005/0177236 A1 | 8/2005 | Mathieu et al. |
| 2005/0187625 A1 | 8/2005 | Wolek et al. |
| 2005/0216059 A1 | 9/2005 | Bonutti |
| 2005/0240267 A1 | 10/2005 | Randall et al. |
| 2005/0240271 A1 | 10/2005 | Zubok et al. |
| 2005/0256574 A1 | 11/2005 | Paul et al. |
| 2005/0267534 A1 | 12/2005 | Bonutti |
| 2006/0085071 A1 | 4/2006 | Lechmann et al. |
| 2006/0129240 A1 | 6/2006 | Lessar et al. |
| 2006/0167495 A1 | 7/2006 | Bonutti |
| 2006/0217809 A1 | 9/2006 | Albert et al. |
| 2006/0235470 A1 | 10/2006 | Bonutti |
| 2006/0265009 A1 | 11/2006 | Bonutti |
| 2007/0088441 A1 | 4/2007 | Duggal et al. |
| 2007/0106388 A1 | 5/2007 | Michelson |
| 2007/0123987 A1 | 5/2007 | Bernstein |
| 2007/0135923 A1 | 6/2007 | Peterman et al. |
| 2007/0162130 A1 | 7/2007 | Rashbaum et al. |
| 2007/0168032 A1 | 7/2007 | Muhanna et al. |
| 2007/0208378 A1 | 9/2007 | Bonutti |
| 2007/0225806 A1 | 9/2007 | Squires et al. |
| 2007/0225810 A1 | 9/2007 | Colleran et al. |
| 2007/0225812 A1 | 9/2007 | Gill |
| 2007/0233253 A1 | 10/2007 | Bray et al. |
| 2007/0250167 A1 | 10/2007 | Bray |
| 2007/0270961 A1 | 11/2007 | Ferguson |
| 2008/0039873 A1 | 2/2008 | Bonutti |
| 2008/0047567 A1 | 2/2008 | Bonutti |
| 2008/0051890 A1 | 2/2008 | Waugh et al. |
| 2008/0051907 A1 | 2/2008 | Marik |
| 2008/0058822 A1 | 3/2008 | Bonutti |
| 2008/0065140 A1 | 3/2008 | Bonutti |
| 2008/0103519 A1 | 5/2008 | Bonutti |
| 2008/0108916 A1 | 5/2008 | Bonutti |
| 2008/0114399 A1 | 5/2008 | Bonutti |
| 2008/0133013 A1 | 6/2008 | Duggal et al. |
| 2008/0140011 A1 | 6/2008 | Bonutti |
| 2008/0140117 A1 | 6/2008 | Bonutti |
| 2009/0076608 A1 | 3/2009 | Gordon et al. |
| 2009/0210062 A1 | 8/2009 | Thalgott et al. |
| 2010/0057206 A1 | 3/2010 | Duffield |
| 2010/0145460 A1 | 6/2010 | Mcdonough |
| 2011/0087327 A1 | 4/2011 | Lechmann |
| 2011/0166658 A1 | 7/2011 | Garber et al. |
| 2011/0251689 A1 | 10/2011 | Seifert |
| 2012/0010623 A1 | 1/2012 | Bonutti |
| 2012/0215226 A1 | 8/2012 | Bonutti |
| 2012/0215233 A1 | 8/2012 | Bonutti |
| 2012/0221017 A1 | 8/2012 | Bonutti |
| 2012/0245690 A1 | 9/2012 | Cowan, Jr. et al. |
| 2013/0110247 A1 | 5/2013 | Doran et al. |
| 2013/0226185 A1 | 8/2013 | Bonutti |
| 2013/0237989 A1 | 9/2013 | Bonutti |
| 2013/0289729 A1 | 10/2013 | Bonutti |
| 2014/0012380 A1 | 1/2014 | Laurence et al. |
| 2014/0018854 A1 | 1/2014 | Bonutti |
| 2014/0025110 A1 | 1/2014 | Bonutti |
| 2014/0025111 A1 | 1/2014 | Bonutti |
| 2014/0025112 A1 | 1/2014 | Bonutti |
| 2014/0039623 A1 | 2/2014 | Iott et al. |
| 2014/0228963 A1 | 8/2014 | Bonutti |
| 2014/0257380 A1 | 9/2014 | Bonutti |
| 2010/4030956 | 10/2014 | Bonutti |
| 2014/0343573 A1 | 11/2014 | Bonutti |

FOREIGN PATENT DOCUMENTS

| | | |
|---|---|---|
| WO | 1999063914 A1 | 12/1999 |
| WO | 2005007040 A1 | 1/2005 |
| WO | 2007098288 A2 | 8/2007 |
| WO | 2008014258 A2 | 1/2008 |

OTHER PUBLICATIONS

M. Spruit et al., The in vitro stabilizing effect of polyetheretherketone cages versus a titanium cage of similar design for anterior lumbar interbody fusion, 14(8) Eur. Spine J. 752, 752-758 (2005).

P. Schleicher et al., Biomechanical comparison of two different concepts for stand alone anterior lumbar interbody fusion, 17(12) Eur. Spine J. 1757, 1757-1765 (2008).

P.W. Pavlov et al., Anterior lumbar interbody fusion with threaded fusion cages and autologous bone grafts, 9 Eur. Spine J. 224, 224-229 (2000).

\* cited by examiner

INTERVERTEBRAL IMPLANT

CROSS-REFERENCE TO RELATED APPLICATIONS

This application is a continuation of U.S. patent application Ser. No. 15/864,447, filed on Jan. 8, 2018, which is a continuation of U.S. patent application Ser. No. 14/848,827, filed on Sep. 9, 2015 (now issued as U.S. Pat. No. 9,895,237), which is a continuation of U.S. patent application Ser. No. 12/756,438, filed on Apr. 8, 2010 (now issued as U.S. Pat. No. 9,155,631), all of which are incorporated in their entireties herein.

FIELD OF THE INVENTION

The present disclosure generally relates to a fixation device for positioning and immobilizing at least two adjacent vertebra.

BACKGROUND OF THE INVENTION

The vertebral spine is the axis of the skeleton on which all of the body parts "hang". In humans, the normal spine has seven cervical, twelve thoracic and five lumbar segments. The lumbar spine sits upon the sacrum, which then attaches to the pelvis, and in turn is supported by the hip and leg bones. The bony vertebral bodies of the spine are separated by intervertebral discs, which act as joints but allow known degrees of flexion, extension, lateral bending, and axial rotation and translation.

The typical vertebra has a thick anterior bone mass called the vertebral body, with a neural (vertebral) arch that arises from the posterior surface of the vertebral body. The central of adjacent vertebrae are supported by intervertebral discs. The spinal disc and/or vertebral bodies may be displaced or damaged due to trauma, disease, degenerative defects, or wear over an extended period of time. One result of this displacement or damage to a spinal disc or vertebral body may be chronic back pain. In many cases, to alleviate back pain from degenerated of herniated discs, the disc is removed along with all or part of at least one neighboring vertebrae and is replaced by an implant that promotes fusion of the remaining bony anatomy.

However, the success or failure of spinal fusion may depend upon several factors. For instance the spacer or implant or cage used to fill the space left by the removed disc and bony anatomy must be sufficiently strong to support the spine under a wide range of loading conditions. The spacer should also be configured so that it likely to remain in place once it has been positioned in the spine by the surgeon. Additionally the material used for the spacer should be biocompatible material and should have a configured that promotes bony ingrowth.

In combination with spacers or cages, a plating system is used to further stabilize the spine during the fusion process. These devices, commonly referred to as bone fixation plating systems, typically include one or more plates and screws for aligning and holding vertebrae in a fixed position with respect to one another. Plating systems independent of the spacers provide additional complications such as loosening and failure of the hardware. Two common failures are the breakage of the plates, and the backing out of screws into soft tissues of the patient's body. The backing out of the screws is typically a result of the screws failure to achieve a sufficient purchase in the bone, although the stripping of the screws has also been known to cause this problem.

Another common problems is that plating systems require "carpentry" work to match fit aspects of the vertebral bodies.

There is a need for a spine stabilization system that promotes fusion of adjacent vertebrae while at the same time provides stabilization of the spinal area where fusion occurs. There is a need for a system that incorporates both the fusion element and the plating element in one system to reduce the possible complications that may occur. There is also a need to provide a system that reduces the complications that may occur in the fusion element and the plating element and a need for this system to be configured so that positioning this system is efficient and easy.

SUMMARY OF THE INVENTION

The present invention provides an intervertebral implant for implantation in a treated area of an intervertebral space between vertebral bodies of a spine. The implant includes a spacer portion having an inferior and superior surface, wherein the inferior and superior surfaces each have a contact area capable of engaging with anatomy in the treated area, and the inferior and superior surfaces define a through-hole extending through the spacer body. The present invention further provides screw holes extending from a side portion to the inferior and superior surfaces of the spacer portion and a plate portion rigidly coupled to the spacer portion through a coupling means, wherein the plate portion contains screws holes for receiving screws. A screw back out prevention mechanism is adapted on the plate portion to prevent the back out of screws from the screw holes and to secure the plate portion to the spacer portion.

DETAILED DESCRIPTION OF THE ILLUSTRATED EMBODIMENTS

Embodiments of the disclosure are generally directed to flexible stabilization systems for use with the anterior, antero-lateral, lateral, and/or posterior portions of at least one motion segment unit of the spine. The systems of the invention are designed to be conformable to the spinal anatomy, so as to be generally less intrusive to surrounding tissue and vasculature than existing rigid stabilization systems.

Certain embodiments may be used on the cervical, thoracic, lumbar, and/or sacral segments of the spine. For example, the size and mass increase of the vertebrae in the spine from the cervical to the lumbar portions is directly related to an increased capacity for supporting larger loads. This increase in load bearing capacity, however, is paralleled by a decrease in flexibility and an increase in susceptibility to strain. When rigid immobilization systems are used in the lumbar segment, the flexibility is decreased even further beyond the natural motion restriction of that segment. Replacing the conventional rigid immobilization systems with certain embodiments disclosed herein may generally restore a more natural movement and provide added support to the strain-susceptible area.

Figure 1:
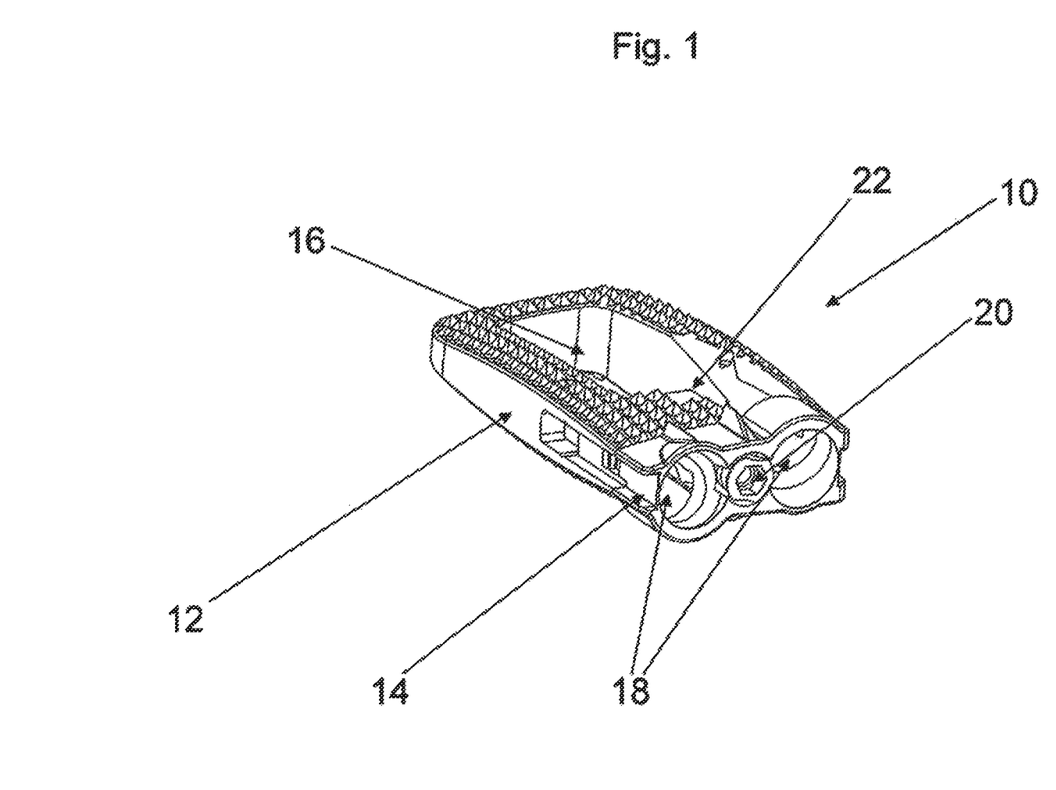
FIG. 1 is a perspective view of one embodiment of an intervertebral implant according to the present invention.

FIGS. 1-4 illustrate the different views of one particular embodiment of the present invention. The intervertebral fusion implant according to the present invention is a stand-alone interbody fusion device used to provide structural stability in skeletally mature individuals following discectomies. These implants are available in various heights and geometric options to fit the anatomically needs of a wide variety of patients. As shown in FIG. 1, implant 10 is generally positioned in the intervertebral space between two adjacent vertebrae. Implant 10 primarily incorporates a spacer portion 12 and a plate portion 14. In this particular embodiment, the spacer portion 12 includes a graft window 16 for the placement of bone graft to enhance fusion between two adjacent vertebrae. The plate portion 14 includes at least one screw hole 18, however, in the preferred embodiment of the present invention, two screw holes 18 are provided. Also, in the plate portion 14 of the implant 10, pin screw 20 is provided. There is also provided a nut 22 which receives the pin screw 20 to secure the spacer portion 12 and the plate portion 14 rigidly to each other. Although a pin screw and a nut are utilized as a blocking mechanism and a plate and spacer attachment mechanism, any other similar type of arrangement can be also utilized.

It should be noted that the titanium plate portion 14 and the spacer portion 12 maybe coupled through any other feasible means such as hooks, screws, and any other type of fastening means. The implant 10 also allows for at least two titanium screws to be inserted at a compound angle for maximum screw purchase into the superior and inferior vertebral bodies. The pin screw 20 is provided on the plate portion 14 to capture the sides of both of the at least two screws preventing the titanium screws from backing out. It should be noted that the present application is not limited to being of a PEEK spacer and a titanium plate. Other materials that are physiologically compatible which are similar and which may be unique to spacers and plates may be utilized in various combinations.

Figure 2:
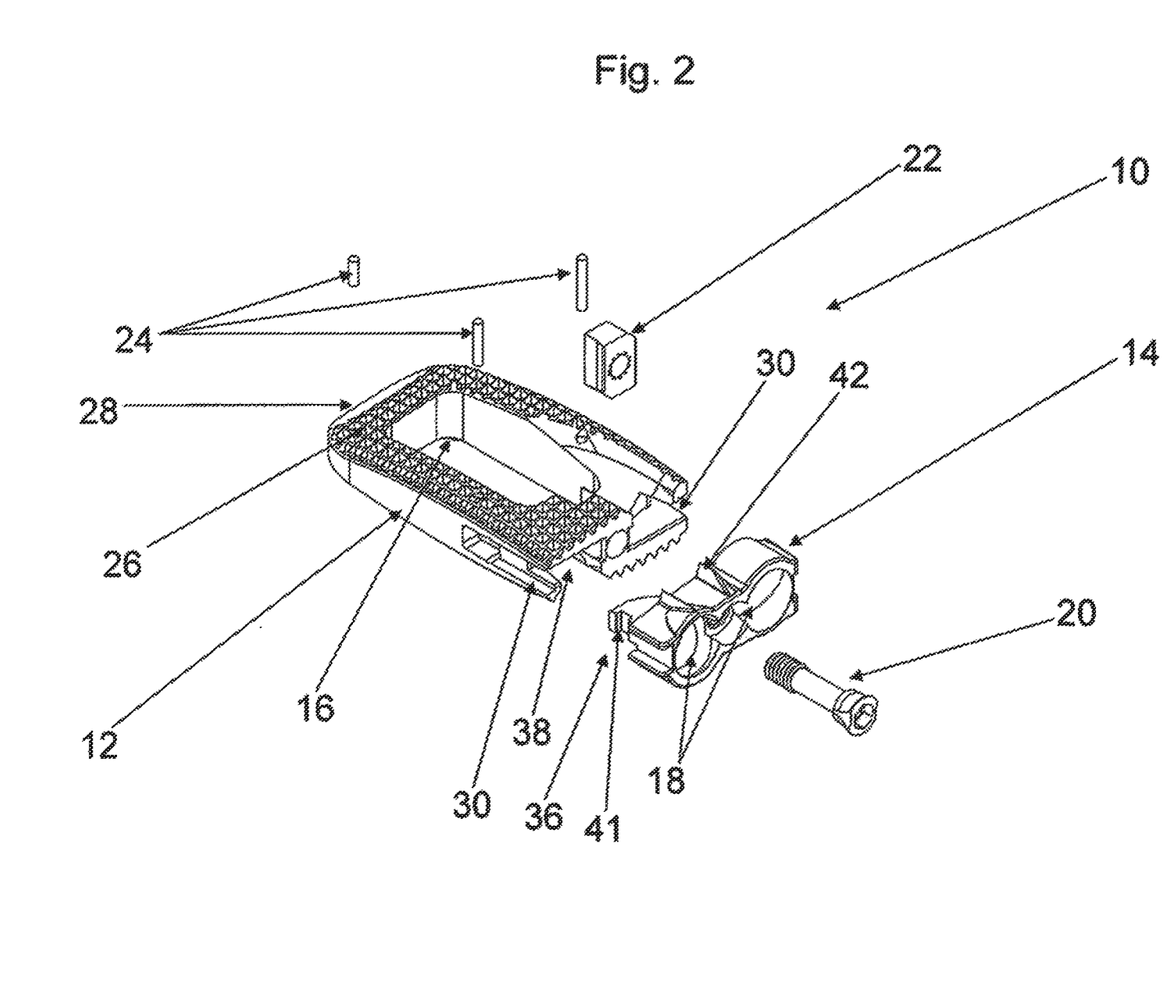
FIG. 2 is an exploded view of the embodiment of the implant shown in FIG. 1.
Figure 3:
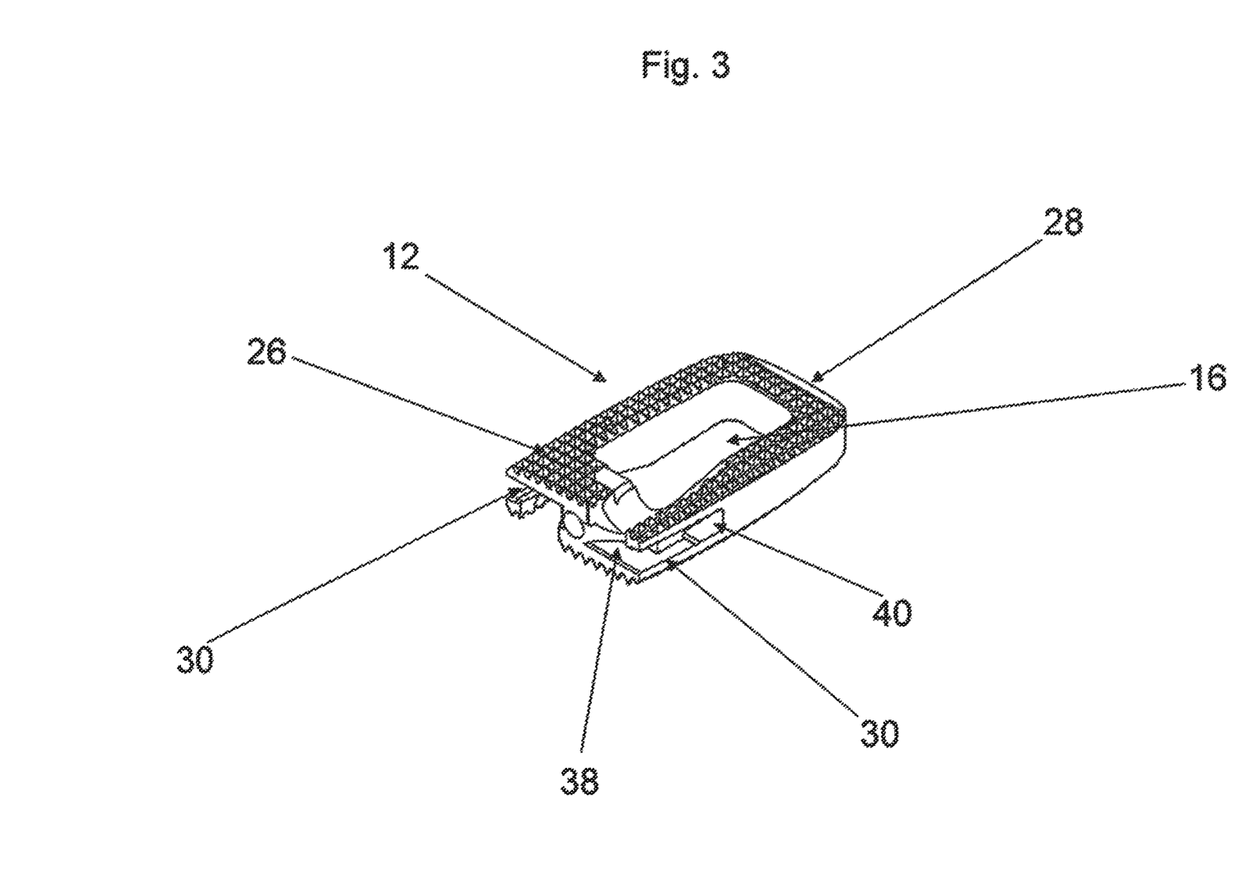
FIG. 3 is a perspective view of the spacer portion of the intervertebral implant of FIG. 1.

In FIGS. 2 and 3, an exploded view of the intervertebral implant 10 and the spacer portion 12 are illustrated in greater detail. The implant 10 comprises the spacer portion 12, plate portion 14, and a pin screw 20 which prevents the back out of the screws as well as securing the plate portion 14 to the spacer portion 12. The spacer portion 12 can be comprised of any material that is conducive to the enhancement of fusion between the two adjacent vertebrae. In one particular embodiment, the spacer portion 12 is made of PEEK material which is physiologically compatible. It should be noted that any other material that are physiologically compatible may also be used. The spacer portion 12 contains tantalum pins 24 that enable radiographic visualization. The spacer portion 12 further comprises superior and inferior portions that are provided with a plurality of pyramidal protrusions 26. The superior and inferior portions of the spacer portion 12 are bi-convex for greater contact with the vertebral endplates of the adjacent vertebrae. The protrusions 26 can be configured to be any size or shape for further anchoring the spacer portion 12 to each of the adjacent vertebrae. Protrusions 26 on the superior and inferior surfaces of each implant grip the endplates of the adjacent vertebrae to aid in expulsion resistance. Although the protrusions 26 of the preferred embodiment are illustrated as being pyramidal, it should be noted that the protrusions 26 may be designed and configured to be any size and shape that further anchors the implant to the adjacent portions of the vertebrae. The spacer portion 12 of the implant also provides a leading edge chamfer 28 which enables self distraction of the vertebral bodies while inserting. It should be further noted that although FIGS. 1-4 illustrate a spacer portion that is elongated so that the implant may be positioned during an lateral access procedure, the spacer portion can be designed and configured to be in shape and configuration for accessing the spine through any access procedure such as an anterior, posterior and/or transforaminal.

The spacer portion 12 is designed and configured to receive an instrument for positioning the implant 10 into the spine. Cutouts 30 are configured on the outer opposing sides of the spacer portion 12. It should be noted that the length and depth of the cutouts are optimally configured to rigidly hold the implant 10 with the instrument with a minimal amount movement when the holder is attached to the implant.

Figure 4:
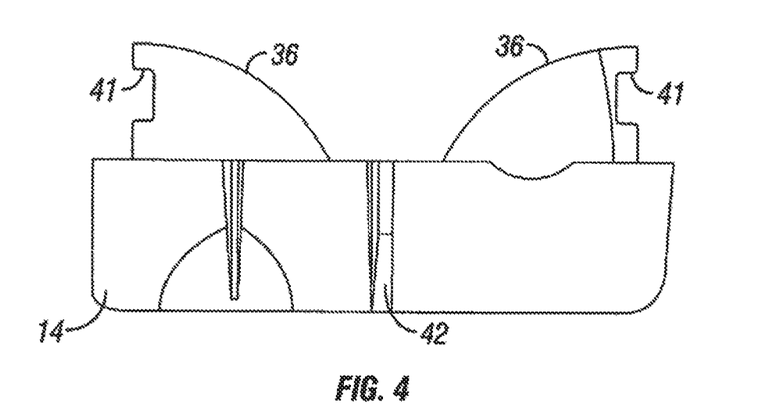
FIG. 4 is a top view of the plate portion of the intervertebral implant of FIG. 1.

Now turning to FIGS. 2 and 4, plate portion 14 will be discussed in greater detail. The plate portion 14 can be comprised of any physiologically compatible material. In the preferred embodiment, the plate portion 14 of the implant 10 is composed of titanium. The plate portion 14 is provided with two screw holes 18. However, it should be noted that implant 10 may be comprised of any amount of screw holes 18. The screw holes 18 are situated both in the spacer portion 12 and the plate portion 14 for receiving bone screws which are attached to the adjacent vertebral bodies at different angles. As shown in FIGS. 2, and 4, the screw holes 18 are configured to receive screws at different angles. One screw hole is configured to direct a bone screw into the superior vertebrae and the second screw hole is configured to direct a second bone screw into the inferior vertebrae. The screws enter the screw holes 18 at specified angles to enter the adjacent vertebral bodies at the optimal locations. The screws are also configured and adapted to provide optimal purchase with the adjacent vertebral bodies.

The plate portion 14 is further provided with a tongue 36 which couples to a first groove 38 within the cutout of the spacer portion 12. As illustrated in FIG. 4, tongue 36 is curved to correspond to the curvature of the first portion of the groove 38 in the spacer portion 12. A second groove 40 in the spacer portion 12 is also positioned on opposing sides of the spacer portion 12. The second groove 40 is independent of the first groove 38. The second groove 40 is designed and configured to receive a portion of an instrument. The plate portion 14 is also provided with a groove 41 within the tongue 36 which is adapted to couple to the instrument. As a result, the instrument may be used to securely attach the spacer portion 12 and the plate portion 14. It should be noted that although the tongue 36 is provided on the plate portion, in alternative embodiments, the spacer portion may contain a tongue and the plate portion configured to receive the tongue in a groove.

The plate portion 14 is also provided with knife-protrusions 42 positioned on the upper and lower portions of the plate portion 14. These protrusions 42 extend into a portion of the upper and lower vertebrae to help stabilize the implant 10. Specifically, these protrusions 42 enable torsional stability of the implant. The plate 14 is also provided with "eye brow" like structure which fully captures the bone screws while still allowing for the screws to reside about the tooth root plane and remaining lower than the tooth (protrusions on the spacer portion 12). The plate 14 geometry allows for the minimum reduction of peek volume. The plate 14 height remains level to the peek tooth root so that compressive loads are always subjected to the peek body where the graft is contained. Compound holes are drilled to accept bone screws and to allow for fixed or variable angle screws. The anti-back out mechanism is engaged so that the screws do not back out of the implant 10.

Figure 5:
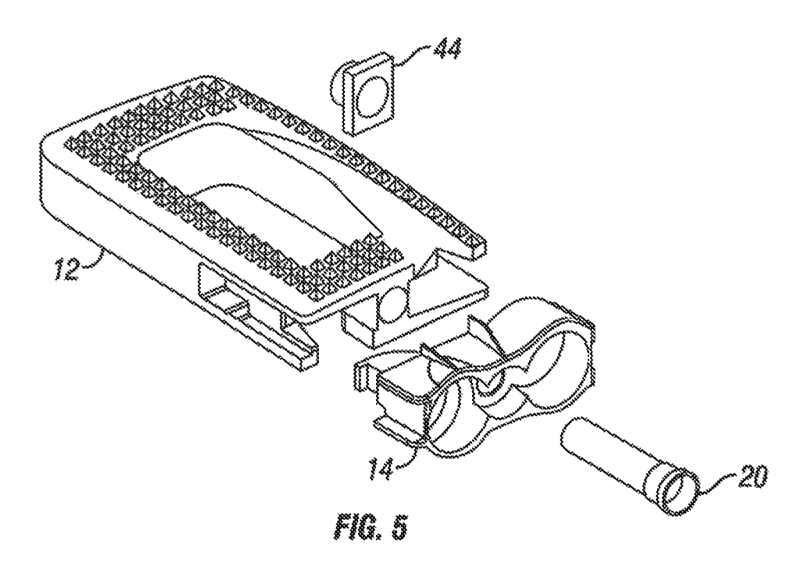
FIG. 5 is an exploded view another embodiment of the present invention.
Figure 6:
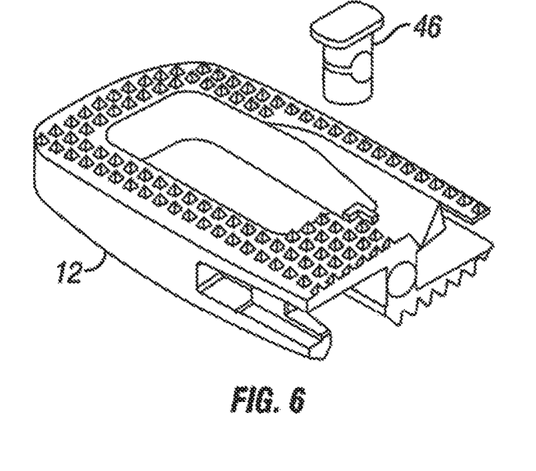
FIG. 6 is a yet another embodiment of a connection element according to the present invention.

Turning back to FIG. 2, the preferred embodiment illustrates the coupling elements 20 and 22 for connecting the plate portion 14 to the spacer portion 12 of the implant 10. Specifically, the pin screw 20 is screwed into the pin hole and as the pin screw is advanced into the threaded portion of the nut 22, the spacer portion and the plate portion are securely attached. FIGS. 5 and 6 illustrate different types of nuts 44, 46 used receive and secure the pin screw to the spacer portion 12. The nut 46 illustrated in FIG. 6 is round and is provided with a mid-line feature to prevent it from backing out. The nut 46 is also flanged with flats to prevent rotation.

FIGS. 7A-7B, 8A-8C, and 9A-9B illustrate different embodiments of a mechanism to attach the plate portion to the spacer portion. FIG. 7 illustrates a plate and spacer comprising a hybrid set screw having threaded and serrated portions. The top threaded portion of the blocking set screw is configured to threaded and serrated portions. The top threaded portion of the blocking set screw may be threaded into the plate while the bottom serrated portion will ratchet into a mating female part that is positioned inside the spacer. Once the serrated portion of the set screw is actuated through threaded internal portion of the spacer, a secure single construct is created.

Figure 8A:
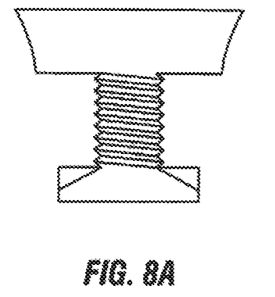
Figure 8B:
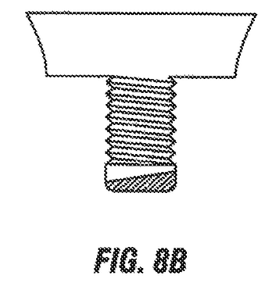
Figure 8C:
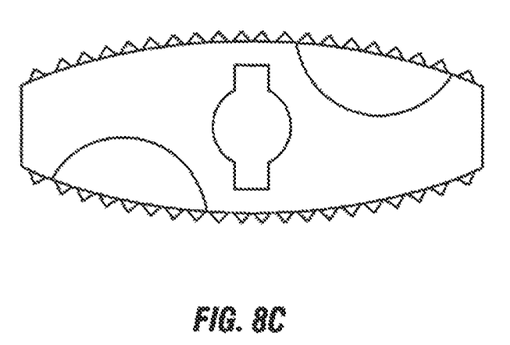

FIGS. 8A-8C illustrates yet another embodiment of a spacer and plate attached via a blocking set screw that is provided with a sloped key at it's distal tip. As the blocking set screw is rotated, the sloped key acts a cam device and clamps the spacer portion and the plate portion together. The blocking set screw may be configured and designed to have one or more sloped keys depending on the clamping force required to securely attach the spacer and the plate portions.

Figure 7A:
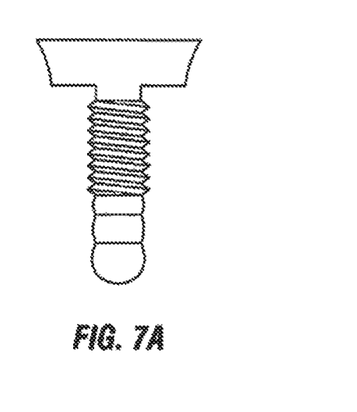
FIGS. 7A-7B, 8A-8C, and 9A-9B illustrate different embodiments for attaching the spacer portion to a plate portion of an intervertebral implant.
Figure 7B:
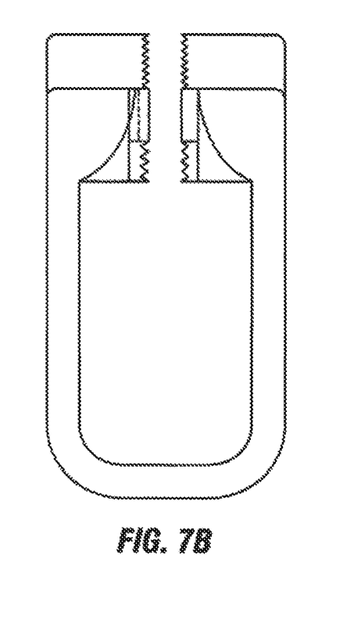
Figure 9A:
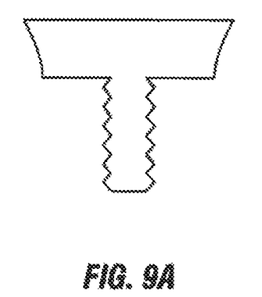
Figure 9B:
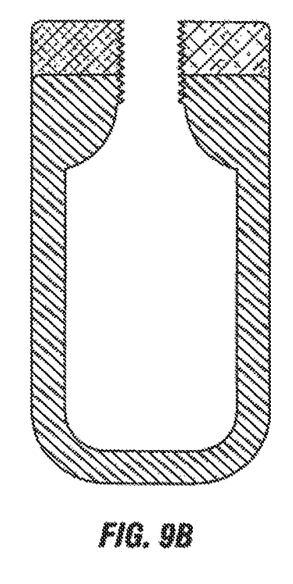

FIG. 9A-9B illustrates yet another mechanism for attaching the spacer portion to the plate portion of an intervertebral implant. In this particular embodiment, the spacer portion and the plate portion are secured via a serrated blocking screw. As the screw is screw is ratcheted through the plate and the spacer, the plate and spacer are secured together. As in the previous embodiments, the spacer portion of FIGS. 7-9 are provided with features such as superior and inferior protrusions, graft hole, and screw holes. Similarly, the plate portions of FIGS. 7-9 are also provided with screw holes for receiving bone screws that secure the spacer and plate portions to the vertebrae.

Now, turning to the method of positioning the implant, it should be noted that the intervertebral implant 10 is positioned in the spine after the disc portion between two vertebral bodies is exposed and removed using rongeurs and other suitable instruments. The posterior and anterior walls of the annulus are generally preserved to provide peripheral support for the implant and graft materials. A trial device attached to a trial holder is then inserted into the disc space to determine size of the implant. This procedure is generally conducted using fluoroscopy and tactile feel. After the appropriate sized implant is selected and attached to an implant holder and drill guide, the implant may be inserted into the disc space. As the surgeon sees fit, the spacer portion of implant may be positioned by itself or the spacer portion and the plate portion may be attached together and then positioned within the spine. If the surgeon chooses to position just the spacer portion, then the spacer portion is positioned within the disc space and graft material is used to pack the graft hole for enhancing fusion of the adjacent vertebrae. If the surgeon decides that additional support is required by attaching the plate portion to the spacer portion, the pin screw is used to attach the spacer portion to the plate portion. Once the plate and the spacer are attached, then the implant is positioned within the disc space. Next, either the combined spacer and plate or just the spacer, the implant is positioned inside the disc space, whereby an awl or any similar type of instrument can be used to drill through the screw hole and break the cortex of the adjacent vertebral body. The surgeon performing this procedure may then use a depth gauge to determine the screw length. Once the appropriate screw length is determined, screws are inserted using a self-retaining screwdriver. After the screws are finally inserted and secured thereby providing solid purchase with the adjacent vertebral bodies, the pin screw anti-back out mechanism is tightened and secured.

In another embodiment of the present invention, the plate portion is not attached to the spacer portion. The spacer portion is positioned within the disc space and bone filler material such bone graft may be delivered directly through the screw holes of the spacer portion into the graft hole. Once the bone filler material is inserted and packed within the spacer portion, a separate plate may be used or in the alternative the spacer portion can be used without the additional plate portion or any other type of plate.

While it is apparent that the invention disclosed herein is well calculated to fulfill the objects stated above, it will be appreciated that numerous modifications and embodiments may be devised by those skilled in the art.

What is claimed is:

1. A method for positioning an intervertebral implant in a treated area of an intervertebral space between vertebral bodies of a spine, said method comprising:
    inserting the implant in the intervertebral space, wherein the implant comprises:
        a spacer having a graft window extending from a superior surface of the spacer to an inferior surface of the spacer;
        a plate coupled to the spacer, wherein the plate includes holes for receiving fasteners; and
        a screw back out prevention mechanism positioned within a recess of the plate and configured to prevent the fasteners from backing out of the holes,
        wherein the screw back out prevention mechanism includes a pin screw and a nut, wherein the nut is configured to be positioned entirely within the graft window of the spacer, and wherein the graft window is configured to receive bone graft to enhance fusion between adjacent vertebrae.

2. The method of claim 1, wherein the at least two fasteners are capable of being inserted into adjacent vertebral bodies at divergent angles.

3. The method of claim 1, wherein the plate further comprises first and second extensions and the spacer comprises first and second recesses.

4. The method of claim 3, wherein the first and second extensions are curved from a center portion of the posterior surface of the plate to a side surface of the plate and correspond to a curvature of the first and second recess of the spacer.

5. The method of claim 1, wherein the plate is capable of being substantially flush with the adjacent vertebral bodies.

6. The method of claim 1, wherein the plate is comprised of metal.

7. The method of claim 6, wherein the metal is comprised of titanium.

8. The method of claim 1, wherein the spacer is comprised of plastic.

9. The method of claim 1, wherein the spacer comprises a plurality of protrusions on superior and inferior surfaces of the spacer.

10. The method of claim 1, wherein the spacer comprises a first hole extending from an anterior surface to the inferior surface of the spacer; and a second hole extending from the anterior surface to the superior surface of the spacer.

11. A method for positioning an intervertebral implant in a treated area of an intervertebral space between vertebral bodies of a spine, said method comprising:
    inserting the implant in the intervertebral space, wherein the implant comprises:
       a spacer having an inferior and superior surface both of which define a graft window extending from the superior surface to the inferior surface of the spacer;
       a plate coupled to the spacer through a pin screw, the plate having an anterior and posterior surfaces, a first and second hole extending from the anterior surface of the plate to the posterior surface of the plate for receiving the first and second fasteners; and
       a nut coupled to the pin screw and positioned on an inner surface of the spacer, wherein the nut is configured to be positioned entirely within the graft window of the spacer, and wherein the graft window is configured to receive bone graft to enhance fusion between adjacent vertebrae.

12. The method of claim 11, wherein the first and second fasteners are capable of being inserted into adjacent vertebral bodies at divergent angles.

13. The method of claim 11, wherein the plate further comprises first and second extensions and the spacer comprises first and second recesses.

14. The method of claim 13, wherein the first and second extensions are curved from a center portion of the posterior surface of the plate to a side surface of the plate and correspond to a curvature of the first and second recess of the spacer.

15. The method of claim 11, wherein the plate is capable of being substantially flush with the adjacent vertebral bodies.

16. The method of claim 11, wherein the plate is comprised of metal.

17. The method of claim 16, wherein the metal is comprised of titanium.

18. The method of claim 11, wherein the spacer is comprised of plastic.

19. The method of claim 11, wherein the spacer comprises a plurality of protrusions on superior and inferior surfaces of the spacer.

20. The method of claim 11, wherein the spacer comprises a first and second hole extending from an anterior side of the spacer to the inferior and superior surfaces of the spacer, wherein the first and second holes are configured to receive a first and second fastener.

* * * * *